United States Patent [19]

Hansen

[11] Patent Number: 5,831,260
[45] Date of Patent: Nov. 3, 1998

[54] HYBRID MOTION TRACKER

[75] Inventor: Per Krogh Hansen, Burlington, Vt.

[73] Assignee: Ascension Technology Corporation, Burlington, Vt.

[21] Appl. No.: 710,025

[22] Filed: Sep. 10, 1996

[51] Int. Cl.$^6$ ............................. G06M 7/00; H01J 40/14; G01S 5/04
[52] U.S. Cl. ........................ 250/221; 250/215; 342/443; 364/559
[58] Field of Search ..................................... 340/551, 555, 340/556; 73/705; 318/480; 356/321, 141.3, 375; 250/206.1, 206.2, 215, 221, 526; 342/443, 448; 364/559

[56] References Cited

U.S. PATENT DOCUMENTS

| | | | |
|---|---|---|---|
| 4,825,020 | 4/1989 | Arimura | 250/231.18 |
| 4,906,846 | 3/1990 | Arimura | 250/229 |

*Primary Examiner*—William L. Oen
*Attorney, Agent, or Firm*—H. Jay Spiegel

[57] ABSTRACT

A hybrid motion tracker captures the motion of a person. Magnetic field sensors and optical sources are placed on a person, each located on different limbs. A fixed transmitter emits electromagnetic energy and infrared light is transmitted from the optical light sources to the fixed optical sensors. The magnetic field sensors sense the magnetic field and a computer calculates each sensor's position and orientation relative to the fixed transmitter. The optical system's Position Sensing Detectors measure the transmitted infrared light and the computer calculates the position and orientation of each optical light source. The position and orientation of each sensor is used to reconstruct the person's motion in real time, which is sent to a host computer. The computer utilizes the optical system which is more precise than the magnetic field system to compensate for the magnetic field system and thereby achieve higher accuracies. The system is a hybrid system using both magnetic fields and infrared light. By combining the two different technologies into one system, all of the advantages of the two systems by themselves are employed and none of their disadvantages become detrimental, in particular, accuracy and dynamic performance are enhanced over results obtained through sole use of a magnetically based system.

12 Claims, 5 Drawing Sheets

HYBRID MOTION TRACKER

BACKGROUND OF THE INVENTION

The present invention relates to a hybrid motion tracker. Multiple sensors are placed on a person, each located on a different limb. Fixed transmitters emit electromagnetic energy and the position and orientation of each sensor is measured and used to reconstruct the person's motion in real time.

Many different position and orientation systems have been developed utilizing AC or DC magnetic fields, infrared light, acoustic waves, etc. Each system has its advantages and disadvantages. The system described herein is a hybrid system using both magnetic fields and infrared light. By combining the two different technologies, a system is made that has all of the advantages of the two systems and none of their disadvantages.

In U.S. Pat. No. 5,422,715 to Thomas L. Clarke, a hybrid orthogonal localization and orientation system is described that uses an optical system to measure the position of a remote object combined with independent tilt and magnetic compass direction sensors to measure the orientation of the same remote object. The system utilizes the optical technology to measure the position only and a separate sourceless technology to measure the orientation only. The system does not combine the measurements of the two different technologies to compensate for any of the disadvantages of any of the two technologies.

In U.S. Pat. No. 4,849,692 and U.S. Pat. No. 4,945,305 to Ernest B. Blood, a remote object's position and orientation are determined. The system utilizes a plurality of pulsed DC magnetic fields with long, fixed length, steady state components. The steady state component of the generated magnetic fields is measured by DC-field sensitive sensors. The system reduces the field distortions resulting from the decay of eddy currents induced in electrically conductive materials by the generated magnetic fields. The Blood system waits a long enough time for the eddy currents to decay substantially, before measuring the steady state component of the generated magnetic fields. Blood teaches a position and orientation system in six degrees of freedom wherein the source is fixed and the sensor is movable. The Blood system suffers from short operation distances and problems with eddy current distortion, if conductive metallic objects are present. The Blood system does not provide any compensation technique, if ferrous metallic objects are present.

In U.S. Pat. No. 5,453,686 to Peter T. Anderson, a remote object's position and orientation are determined. The Anderson system utilizes a plurality of pulsed magnetic fields with long, fixed length, steady state components. The steady state component of the generated magnetic fields is measured by passive sensors. The system reduces the field distortions resulting from the decay of eddy currents induced in electrically conductive materials by magnetic fields. The Anderson system waits a long enough time for the eddy currents to decay substantially, before measuring the steady state component of the generated magnetic fields. Anderson teaches a position and orientation system in six degrees of freedom. The source is fixed and the sensor is movable. The system suffers from short operation distances and problems with compensation for eddy current distortion, if conductive metallic objects are present. The system does not offer any compensation technique, if ferrous metallic objects are present.

The following additional prior art, directed to magnetic field systems, is known to Applicant:

U.S. Pat. No. 3,868,565 to Kuipers
U.S. Pat. No. 3,983,474 to Kuipers
U.S. Pat. No. 4,054,881 to Raab
U.S. Pat. No. 4,287,809 to Egli et al.
U.S. Pat. No. 4,298,874 to Kuipers
U.S. Pat. No. 4,314,251 to Raab
U.S. Pat. No. 4,328,548 to Crow et al.
U.S. Pat. No. 4,346,384 to Raab
U.S. Pat. No. 4,393,831 to Egli et al.
U.S. Pat. No. 4,396,885 to Constant
U.S. Pat. No. 4,710,708 to Rorden
U.S. Pat. No. 4,737,794 to Jones
U.S. Pat. No. 4,742,356 to Kuipers
U.S. Pat. No. 4,819,250 to Rotier
U.S. Pat. No. 5,307,072 to Jones
U.S. Pat. No. 5,457,641 to Zimmer et al.

In each of the above-listed patents, Alternate Current (AC) magnetic fields are transmitted from a fixed source and are received at a movable sensor. A processor calculates the position and orientation of the sensor, relative to the fixed source, from measurements of received magnetic fields.

All of the above-listed patents disclosing use of AC magnetic fields teach a position and orientation system in up to six degrees of freedom. In each case, the source is fixed and the sensor is movable. The systems suffer from short operation distances and serious problems with eddy current distortion, if conductive metallic objects are present. The systems do not offer any compensation technique, if ferrous metallic objects are present.

U.S. Pat. No. 3,375,375 to Abbey et al. discloses the use of two rotating scanners generating optical fan-shaped beams as well as sensors attached to the object to be measured, specifically a pilot's helmet. This two scanner system is necessary merely to compute the line-of-sight (LOS) to the pilot's helmet.

U.S. Pat. No. 4,818,107 to Ono et al. discloses a system for measuring the position of a moving body. The system utilizes two fixed scanning laser beams with separate origins and three photodetectors on the moving body. The system uses triangulation and measures only the position (x,y,z) and the attitude angle.

U.S. Pat. No. 4,896,962 to Menn et al. discloses a system for determining the spatial location and the line-of-sight of a person wearing a helmet. The system utilizes at least four LEDs placed on the helmet and a fixed two-dimensional array of photoelectric elements. A spherical lens is placed in front of the detector in order to focus the light from the LEDs onto the detector. The work area of this system is limited to the coverage of the lens.

U.S. Pat. No. 4,911,548 to Keren-Gill discloses a system that employs multiple scanners for the origination of multiple fan-shaped optical beams. The scanning mechanism is extremely complicated and cumbersome, and requires precise synchronization between the scanners in order to maintain measurement accuracy.

U.S. Pat. No. 5,128,794 to Mocker et al. discloses a system for measuring the helmet mounted sight of a pilot. The system utilizes at least two laser scanning units with different origins. The system utilizes at least two motors and further utilizes passive reflective markers on the pilot. Mocker et al. only measure the pilot's line-of-sight.

U.S. Pat. No. 5,208,641 to Mocker et al. discloses a system for also measuring the helmet mounted sight of a pilot. The system utilizes a laser cavity and at least three laser detectors. The system further utilizes passive reflective markers on the pilot but only measures the pilot's line-of-sight.

All of the above-discussed optical patents measure the position and orientation in various degrees of freedom. None of them disclose operation if an object is placed between the source and the sensor. All of them require a clear line-of-sight.

The commercial optical systems placed on the market by Motion Analysis Corporation, Santa Rosa Calif., Vicon system by Oxford Medilog Inc., Clearwater, Fla., The Selspot system by Selspot AB Molndal, Sweden, and the Optotrack system by Northern Digital Inc., Waterloo, Ontario, Canada, all measure the position and orientation of an object in various degrees of freedom. However, none of them can operate if an object is placed between the source and the sensor, since all require a clear line-of-sight.

The prior art optical systems are also subject to interference from extraneous sources such as ambient light or electrical sources and, as such, are prone to error, or, at minimum, severe limitations in system flexibility and complicated operation schemes.

Prior art magnetic or optical positioning systems clearly demonstrate the need for a system that will overcome the inherent limitations with range and metallic objects in the magnetic systems and the inherent limitation with shadowing by objects between the source and sensors in the optical systems. The need for such a system was the impetus for the development of the present invention, a hybrid magnetic/optical system, as described herein.

SUMMARY OF THE INVENTION

Accordingly, it is an object of the present invention to provide a unique and enhanced technique for combining a magnetic field system with an optical system in order to achieve the advantages of both systems and none of their disadvantages. This is done in order to provide a superior position and orientation system for the accurate determination of the position and orientation of an object relative to a fixed reference point in six degrees of freedom under all circumstances.

According to a broad aspect of this invention, there is provided a technique of determining the motion of multiple sensors placed on a person in order to determine the motions of the person's extremities in real time, including the following aspects:

1) Placing multiple magnetic field sensors on a person, generating a magnetic field from a fixed source, measuring the received magnetic fields, processing these signals into position and orientation data for each sensor and translating this data into the person's motion.

2) Placing multiple optical sources on a person, generating infrared light from the sources, measuring the received infrared light, processing these signals into position and orientation data for each source and translating this data into the person's motion. Alternatively, the sources could be in a fixed location with the sensors placed on the person.

3) Combining the two systems with a processing means that will:

a) utilize the magnetic field system, when the optical system is not operating due to shadowing, b) utilize the optical system when the magnetic system is not operating due to large metallic distortion, c) utilize the measured position and orientation data by the optical system to correct for errors in the magnetic field system due to metallic distortion, d) utilize the compact magnetic field sensors to measure both the position and orientation and the optical sensors to only measure the position, and e) utilize the high precision and long range of the optical system to compensate for the magnetic field system's degrading Signal-To-Noise ratio and thereby increase accuracy in order to achieve higher total accuracy for the hybrid system.

Accordingly, it is a first object of the present invention to provide a hybrid system and method for determination of the position and orientation of multiple sensors in six degrees of freedom.

It is a further object of the present invention to provide such a system and method that can track the motion of one or more persons.

It is a still further object of the present invention to provide such a system and method which combines a magnetic field system with an optical system.

It is a yet further object of the present invention to provide such a hybrid system that will overcome all the inherent limitations of each system by itself and achieve all of the advantages of each system taken alone.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
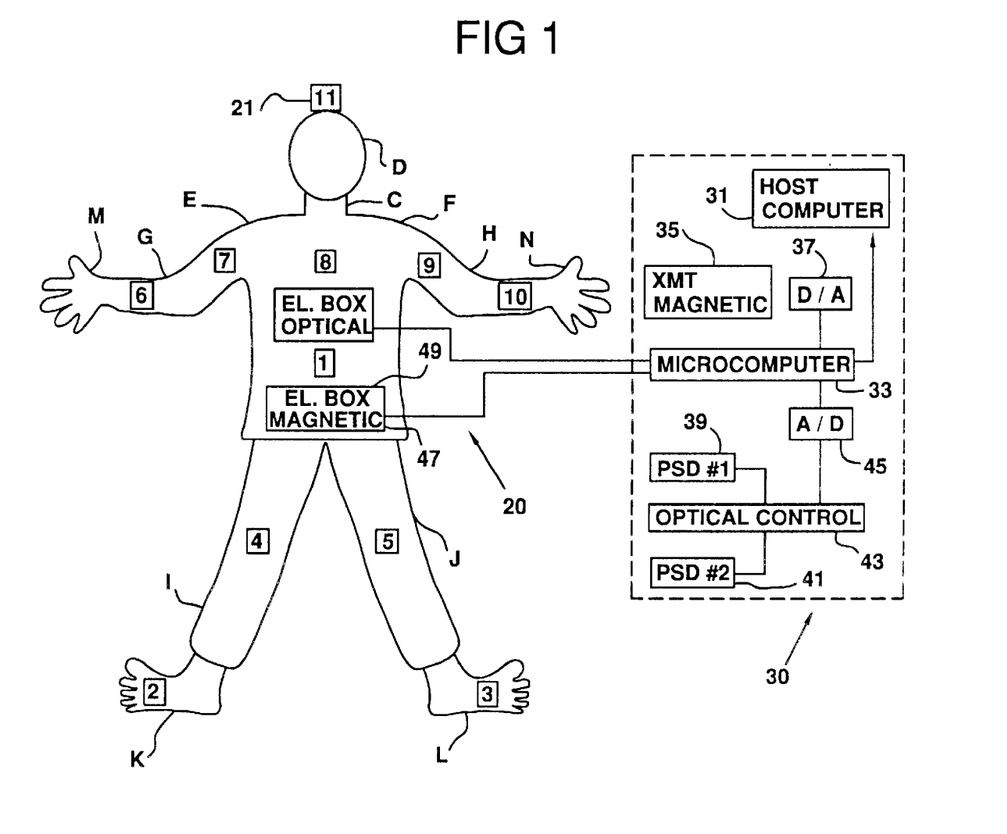
FIG. 1 shows a schematic representation of the inventive system with both optical and magnetic field sensors on a person.

With reference, first, to FIG. 1, a schematic representation of a person is generally designated by the reference letter A and, of course, includes an abdomen B, neck C, head D, shoulders E, F, arms G, H, legs I, J, feet K, L, right hand M, left hand N, and chest O. The inventive system is generally designated by the reference numeral 20 and is seen to include, preferably, eleven sensors numbered 1–11 and placed at various strategic locations on the body of the person A. The locations of the sensors 1–11 are shown in Table 1 below as follows:

TABLE 1

| Sensor Number | Body Location |
|---|---|
| 1 | Abdomen B |
| 2 | Right Foot K |
| 3 | Left Foot L |
| 4 | Right Leg I |
| 5 | Left Leg J |
| 6 | Right Hand M |
| 7 | Right Arm G |
| 8 | Chest O |

TABLE 1-continued

| Sensor Number | Body Location |
| --- | --- |
| 9 | Left Arm H |
| 10 | Left Hand N |
| 11 | Head D. |

Figure 2:
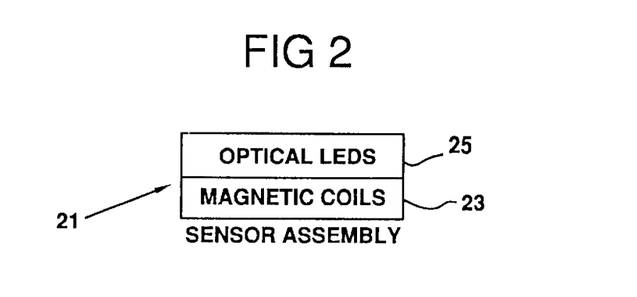
FIG. 2 shows a sensor assembly, consisting of both an optical sensor and a magnetic field sensor.

A typical source/sensor assembly is depicted in FIG. 2, is representative of the sensors 1–11, and is designated by the reference numeral 21. The source/sensor assembly is seen to include a magnetic sensor 23 consisting of three mutually orthogonal magnetic coils and an optical source 25 which, in fact, preferably consists of an omnidirectional optical transmitter including one or more light emitting diodes that preferably transmit infrared light to position sensing detectors as will be described in greater detail hereinafter.

Referring back to FIG. 1, the inventive system includes a fixed base unit 30 that includes a host computer 31 and control means comprising a microcomputer 33. The microcomputer 33 is connected to a magnetic transmitter 35 via a digital-to-analog (D/A) converter 37. The magnetic transmitter 35 consists of three mutually orthogonal coils.

With further reference to FIG. 1, the base unit 30 includes two position sensing detectors 39 and 41 that are interconnected to the microcomputer 33 via an optical receiver 43 and an A/D converter 45. As should now be understood, under the control of the microcomputer 33, the magnetic transmitter 35 transmits magnetic signals that are received by the magnetic sensors 23. In one preferred mode of operation of the magnetic transmitter 35, the magnetic transmitter 35 consists of three mutually orthogonal magnetic coils described as an x-axis coil, a y-axis coil, and a z-axis coil. Under the control of the microcomputer 33, each of these coils is individually activated sequentially and these activations are sensed by the mutually orthogonal coils of the magnetic sensors 23, with signals corresponding to receipt of magnetic energy from each individual coil being sent from each magnetic sensor 23 via a magnetic electric box 47 mounted on the person A to the microcomputer 33 where position and orientation in six degrees of freedom may be calculated.

Concurrently, the optical transmitter 25 transmits pulses of infrared light that are received by the position sensing detectors 39, 41 on the active areas thereof whereupon signals indicative of position and orientation are sent to the optical receiver 43 and thence to the microcomputer 33 via the A/D converter 45. Another electrical box 49 is mounted on the person A and receives control signals from the microcomputer 33 to control pulsing of the optical transmitter 25. In the preferred embodiment of the present invention, the position sensing detectors 39, 41 consist of charge coupled devices (CCDs) that are known for their high Signal-To-Noise ratio and, thus, a high degree of measurement accuracy.

In one preferred embodiment of the present invention, each optical transmitter 25 consists of three light emitting diodes arranged in a triangular pattern. When such an arrangement is employed, the optical sub-system of the present invention can measure not only position but orientation of each light emitting diode.

If desired, the operation of the optical sub-system of the present invention may function as described in U.S. Pat. No. 5,422,715 to Clarke. However, if desired, any known optical system or acoustical system or any measuring system utilizing line-of-sight position and orientation measurements may suitably be employed as or in place of the optical sub-system.

The optical sub-system is advantageous due to its high accuracy and its ability to operate at long distances. Its disadvantages include known "shadowing" effects and the complexity of the sensors that are employed if orientation of the sensors must be measured. The user becomes aware that "shadowing" effects are occurring when a light source is pulsed but the detector fails to detect light. Again, as explained above, three omnidirectional light emitting diodes arranged in a triangular pattern will permit measurement of orientation. Of course, if each light emitting diode does not have a clear line-of-sight to the position sensing detectors, then that LED's position and orientation cannot be measured.

Concerning the magnetic sub-system of the present invention, this sub-system does not exhibit "shadowing" effects. Thus, the magnetic system makes up for this deficiency in the optical magnetic sub-system. Also, even where orientation is to be measured, the magnetic sensors 23 may be made extremely compact. This makes up for the deficiency of the optical sub-system concerning the complexity of the optical transmitters 25.

However, the magnetic sub-system exhibits degraded performance when proximate to metallic objects that cause generation of eddy current distortions. The magnetic field attenuates proportional to $1/d^3$ so that the signal-to-noise ratio degrades rapidly as the distance increases gradually. Applicant has found that the magnetic sub-system of the present invention generally exhibits good accuracy only up to a distance of 10 feet between the transmitter and the sensors. In the preferred embodiment of the present invention, the magnetic sub-system may employ either AC or DC magnetic fields or a combination thereof.

Figure 3:
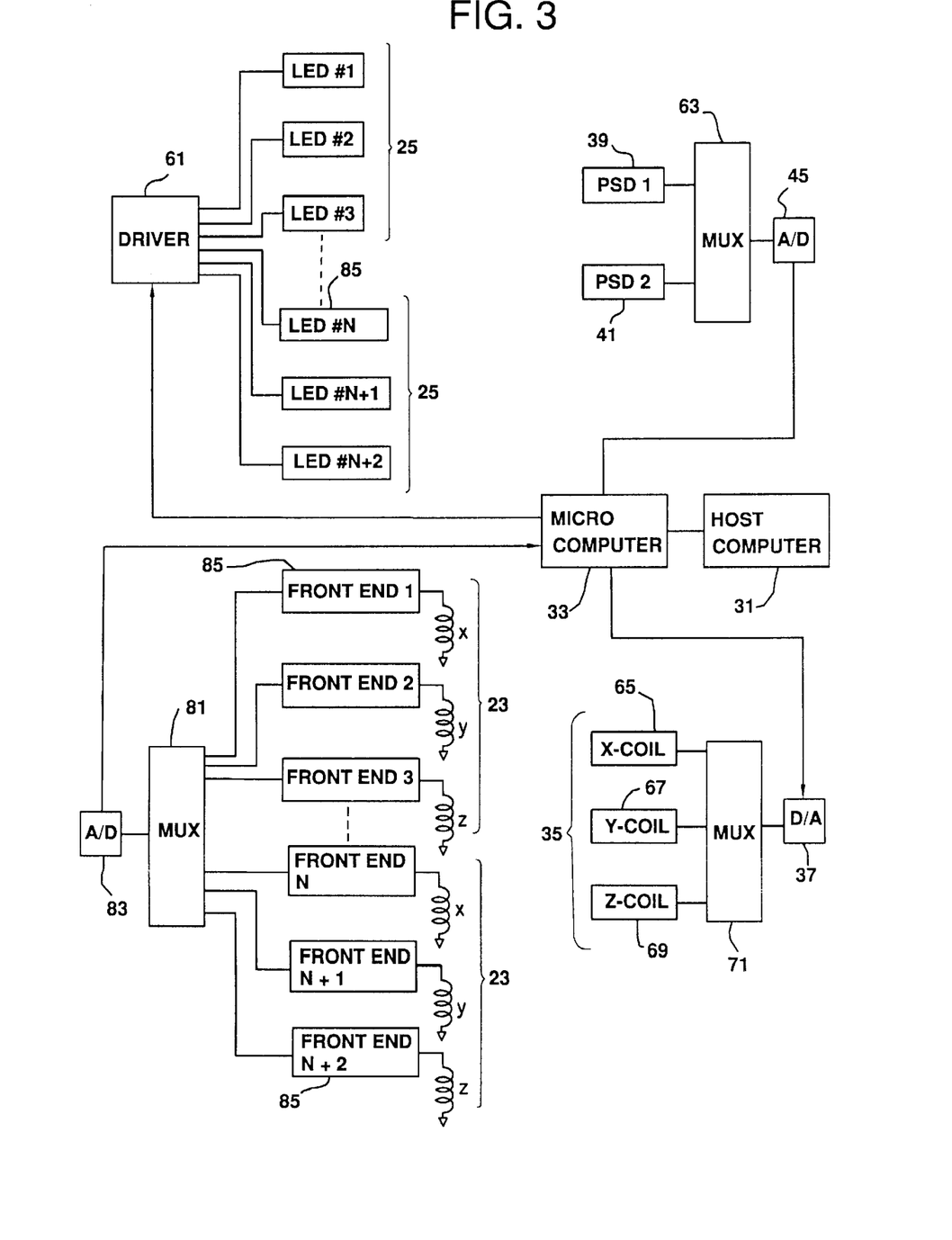
FIG. 3 shows a block diagram for the inventive system.

FIG. 3 shows an electronic block diagram for the preferred embodiment of the present invention and explains how the optical sub-system and the magnetic sub-system are combined together into an integrated system. The driver 61 for the optical transmitters 25 may suitably be located within the electrical box 49 and may receive control signals from the microcomputer 33 in any desired manner such as, for example, via wireless transmission. The multiplexer 63 may be located within the optical receiver 43 and allows sequential transmission of signals received by the position sensing detectors 39 and 41. In the preferred embodiment of the present invention, the optical sub-system may consist of that which is commercially available from Northern Digital and known as the "OPTOTRACK SYSTEM".

As explained above, the magnetic transmitter 35 includes three mutually orthogonal coils 65, 67 and 69. Control signals from the microcomputer 33 are transmitted to the coils 65, 67, 69 via the D/A converter 37, as explained above, and the multiplexer 71 that facilitates sequential operation of each coil 65, 67, 69. As also explained above, each of the magnetic sensor coils 23 consists of three mutually orthogonal coils, an x-coil 75, a y-coil 77, and a z-coil 79. As each of the transmitter coils 65, 67, 69 are sequentially activated, signals received by the various x, y and z-coils of the magnetic sensors 23 are transmitted to the microcomputer 33 with a multiplexer 81 facilitating sequential transmission of signals from each individual coil to the microcomputer 33 via an A/D converter 83. The multiplexer 81, A/D converter 83 and the front end processors 85 may be contained within the electrical box 47. In the preferred embodiment of the present invention, the magnetic sub-system may be that which is described in U.S. Pat. Nos. 4,849,692 and 4,945,305 to Blood.

Figure 4:
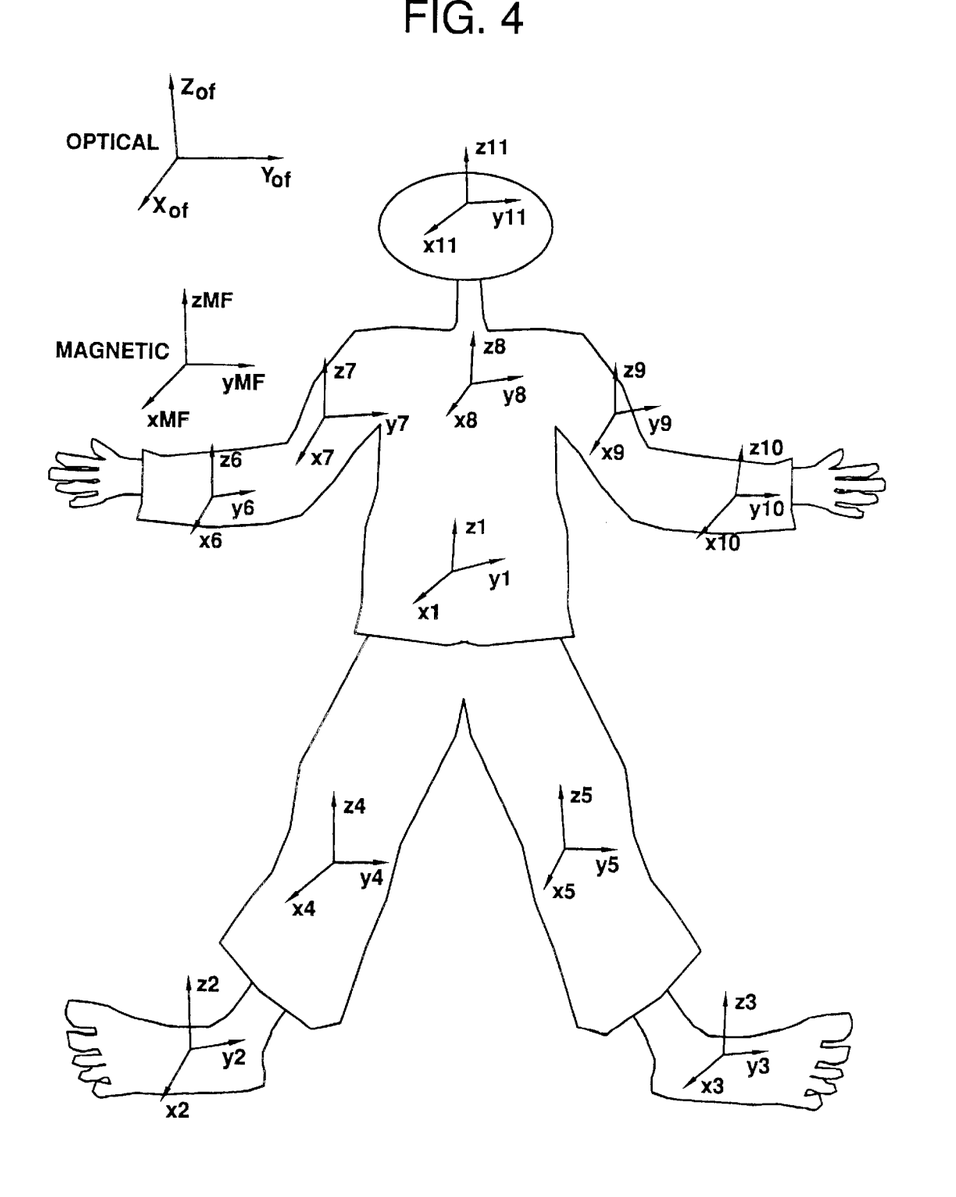
FIG. 4 shows the geometry of the optical and magnetic sub-systems.

FIG. 4 shows the geometry of both the optical and magnetic sub-systems of the present invention. In each case, the fixed portion thereof defines the reference coordinate system that is employed in conducting measurements and interpreting data. The position and orientation of each sensor is measured relative to the fixed reference coordinate system.

Figure 5:
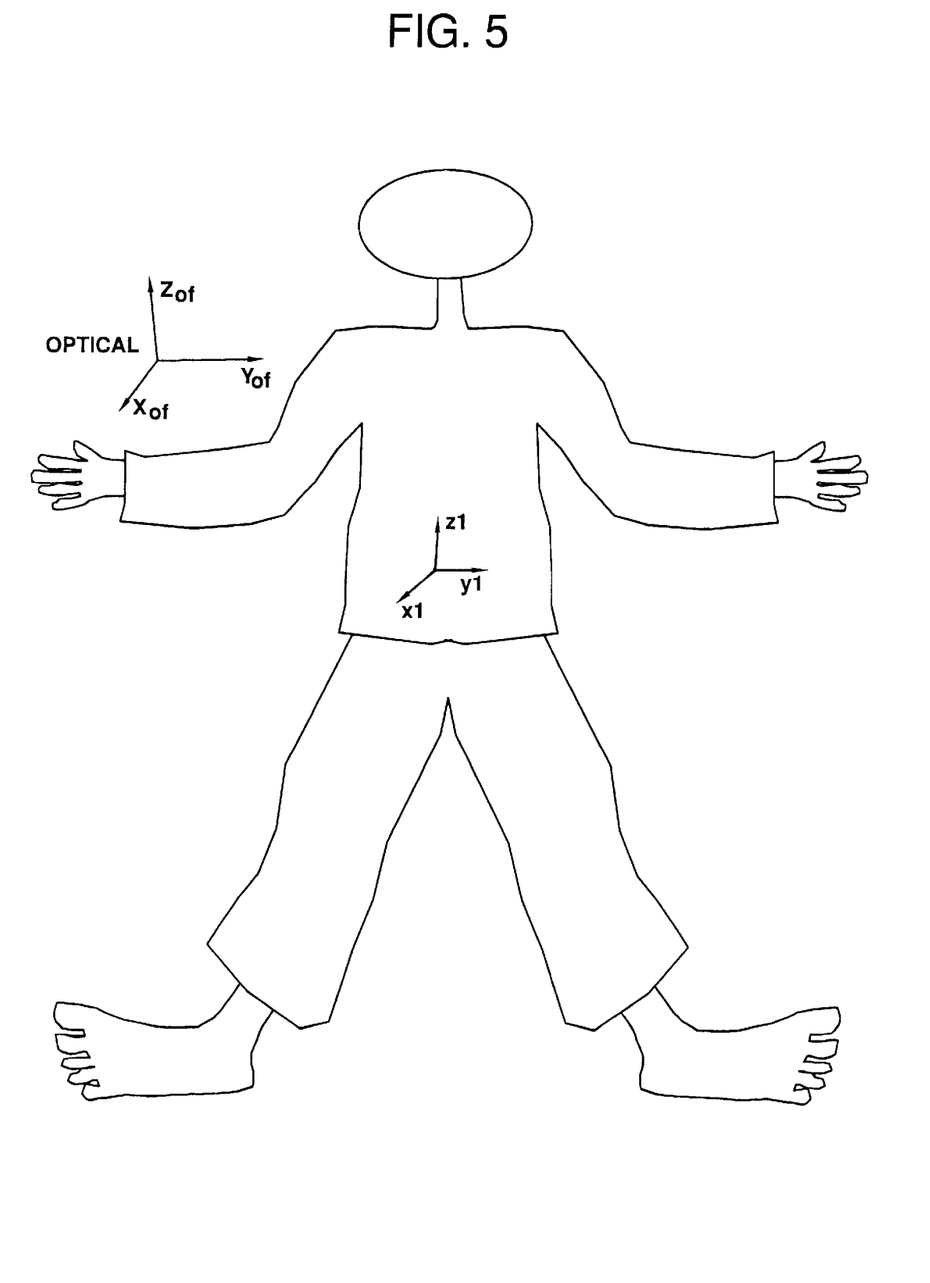
FIG. 5 shows the geometry of the motion capture system thereof.

FIG. 5 shows the geometry of the entire inventive system with its fixed reference coordinate system. This reference coordinate system is defined by the fixed portion of the optical sub-system. All of the continuous corrections that are made to position and orientation of each magnetic and optical sensor are made with respect to the reference coordinate system as depicted in FIG. 5. From knowledge of the position and orientation of each of the various sensors, one may track motions of the person A including motions of all of the limbs, the head, chest, and abdomen. In the preferred embodiment, the algorithms employed may be those which are used in commercially available software packages known as "ALIAS/WAVEFRONT" and "SOFTIMAGE" motion capture software, which software packages are designed to allow motion capture.

Figure 6:
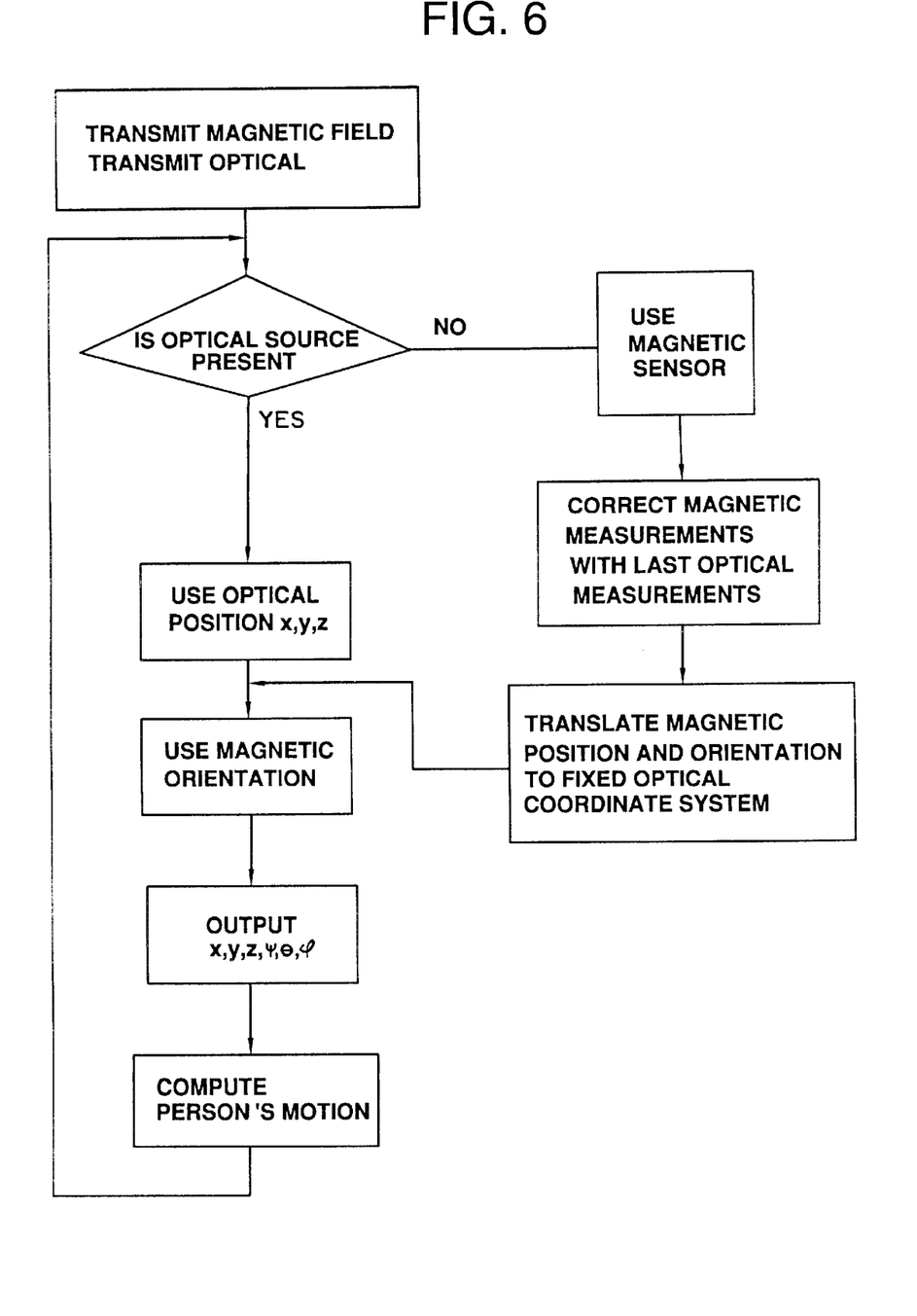
FIG. 6 shows the software control scheme for the inventive system.

FIG. 6 shows the software algorithm used to control the combined system 20. The optical system has better accuracy than the magnetic system and its measurements are used whenever there is no shadowing effect. The optical system is normally only used to measure the position, since to measure the orientation will require a triangular pattern of at least three LEDs for each sensor, and all will need to have clear lines-of-sight. Of course, if desired, where the budget permits, orientation may be measured by the optical sub-system by employing at least a triangular pattern of three omnidirectional light emitting diodes for each sensor. The magnetic system is therefore normally used to measure the orientation. Since both the optical and the magnetic sub-systems are measuring the position of each sensor and since the optical system measures with a higher accuracy, the optical data is used to compensate the magnetic field measurements for first position and then orientation. This will result in higher accuracy for the hybrid system than the magnetic field system could provide alone and also for the orientation measurements. This will especially be helpful when metallic objects are present in the environment which will distort the magnetic system's measurements through generation of eddy current caused distortions.

The optical system has a greater range than the magnetic system. The optical system's measurements will therefore also be helpful in compensating the measurements from the magnetic field system as the magnetic system's performance degrades with the inverse cube of the distance beyond about 10 feet.

Both the optical and the magnetic sub-systems are set up to operate and measure the position and orientation of the sensors. If the optical sensor is employed, meaning that there is no shadowing effect, the actual position of a sensor may be used to measure the position of the sensor. If the optical sensor is not used where shadowing effects are exhibited, the magnetic system is used to find the position. The position is then corrected by the knowledge of the last position obtained for that sensor with the optical system and the difference of that position to the measured position with the magnetic system. The knowledge of the difference in positions measured with the optical system and the magnetic system for the other sensors are also used in the correction.

The magnetic system is then used to find the orientation of each sensor. The orientation is corrected by using the correction factors found from reverse solution of the position of the magnetic system by using the optical position data. The reverse equations are found from the position algorithm disclosed in the Blood patents. The system then outputs the corrected position and orientation data to the host computer.

For a motion capture system, all of the measurements of the individual sensor's position and orientation are translated into the person's motion from the knowledge of where each sensor is placed on the person. A stick figure display will then be representative of the person's motion.

As should be understood by one skilled in the art, more than one person's motion can be measured and shown on the display at the same time. Where the position and orientation of sensors on more than one person are to be measured and displayed, the system 20 must be augmented to provide appropriate multiplexers to allow sequential transmission of position and orientation data to the microcomputer 33.

As should be further understood by one skilled in the art, any number of sensors may be mounted on any person so that motions of various portions of the person may be suitably tracked depending upon those motions that are of interest to the system operator. Interconnection between the various sensors 21 and the base unit 30 may, if desired, be through an electrical conductor or, alternatively, by wireless interconnection in a manner well known to those skilled in the art.

The magnetic field sub-system used in the preferred embodiment utilizes DC magnetic fields and is described in the Blood patents. As should be understood by those skilled in the art, any other magnetic field sub-system utilizing either AC or DC magnetic fields, or both, may be suitably employed.

As explained above, the optical sub-system employed in the preferred embodiment of the present invention may be a system such as that which is made commercially available by Northern Digital Systems and is known as the "OPTOTRACK SYSTEM". Of course, alternatively, any other optically based position measurement system may be employed. As an alternative, the light sources may be located in a fixed location and the light sensors may be affixed to the person whose movements are being monitored. In any case, the coordinate system used in measurements made by each sub-system is defined about the fixed portion of the sub-system. Also, alternative technologies such as those employing infrared light, electromagnetic waves, acoustic waves, etc., could be used instead of the optical sub-system.

The magnetic field sub-system is considered the principal sub-system and measures both position and orientation of all the sensors on the person. The secondary sub-system, here the optical sub-system, can measure both position and orientation of all the sensors on the person provided each optical transmitter consists of at least three light emitting diodes arranged in a triangular pattern. It may, however, in some cases, be only necessary to measure the position of all the sensors on the person. It may, in some cases, only be necessary to measure the position of selected sensors and, in the extreme case, only of one of the sensors.

Accordingly, an invention has been disclosed in terms of preferred embodiments thereof which fulfill each and every one of the objects of the present invention as set forth hereinabove and provides a new and useful hybrid motion tracker, which utilizes the best features of a magnetic field position and orientation system and an optical position and orientation system, of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A hybrid motion tracker system for tracking motions of a person, comprising:

a) a magnetic sensor mounted on a person;

b) a fixed source of magnetic field;

c) an optical source of light mounted on the person adjacent said magnetic sensor;

d) an optical sensor located adjacent said fixed source of magnetic field;

e) a control means for controlling operation of said fixed source of magnetic field and optical source, said control means activating said fixed source of magnetic field and said optical source, said magnetic sensor sensing said magnetic field and sending first signals to said control means indicative of position and orientation of a portion of the person to which said magnetic sensor is affixed, said control means concurrently activating said optical source of light, said optical sensor sensing light from said source of light and, responsive thereto, sending second signals to said control means indicative of, at least, position of said portion of said person.

2. The system of claim 1, further wherein said magnetic sensor comprises three mutually orthogonal sensor coils.

3. The system of claim 2, wherein said source of magnetic field comprises three mutually orthogonal source coils, said control means being adapted to sequentially pulse said source coils one at a time.

4. The system of claim 1, wherein said optical source comprises an optical light source.

5. The system of claim 4, wherein said optical light source comprises a LED.

6. The system of claim 4, wherein said optical light source comprises three LEDs arranged in a triangular pattern.

7. The system of claim 1, including a plurality of magnetic sensors and a corresponding plurality of optical sources of light mounted on a person.

8. The system of claim 4, further wherein said control means includes means for sensing shadowing effects during operation of said optical sensor.

9. The system of claim 4, wherein said optical sensor comprises a plurality of position sensing detectors.

10. The system of claim 9, wherein each position sensing detector comprises a charge coupled device (CCD).

11. The system of claim 4, wherein position and orientation measured by the optical source and sensor comprise means for improving system accuracy.

12. The system of claim 4, wherein position and orientation measured by the optical source and sensor comprise means for improving system dynamic performance.

* * * * *